(12) United States Patent
Lee et al.

(10) Patent No.: US 11,299,771 B2
(45) Date of Patent: Apr. 12, 2022

(54) ENHANCED DNA SENSING VIA CATALYTIC AGGREGATION OF GOLD NANOPARTICLES BY DNA HYBRIDIZATION CHAIN REACTION

(71) Applicants: Jeunghoon Lee, Boise, ID (US); Bernard Yurke, Boise, ID (US); Elton Graugnard, Boise, ID (US); Will Hughes, Blacksburg, ID (US); Bert Huttanus, Blacksburg, VA (US)

(72) Inventors: Jeunghoon Lee, Boise, ID (US); Bernard Yurke, Boise, ID (US); Elton Graugnard, Boise, ID (US); Will Hughes, Blacksburg, ID (US); Bert Huttanus, Blacksburg, VA (US)

(73) Assignee: Boise State University, Boise, ID (US)

( * ) Notice: Subject to any disclaimer, the term of this patent is extended or adjusted under 35 U.S.C. 154(b) by 400 days.

(21) Appl. No.: 15/877,128

(22) Filed: Jan. 22, 2018

(65) Prior Publication Data

US 2018/0216158 A1    Aug. 2, 2018

Related U.S. Application Data

(62) Division of application No. 14/211,076, filed on Mar. 14, 2014, now Pat. No. 9,914,960.

(60) Provisional application No. 61/789,692, filed on Mar. 15, 2013.

(51) Int. Cl.
*C12Q 1/68*    (2018.01)
*C12Q 1/682*   (2018.01)

(52) U.S. Cl.
CPC .................. *C12Q 1/682* (2013.01)

(58) Field of Classification Search
None
See application file for complete search history.

(56) References Cited

U.S. PATENT DOCUMENTS

2006/0234261 A1   10/2006   Pierce et al.
2013/0236880 A1    9/2013   Abduo et al.

OTHER PUBLICATIONS

Ahern, Holly; The Scientist, vol. 9, No. 15, 1995, from the internet: pp. 1-5.*
Jin (Jin et al; JACS, vol. 125, pp. 1643-1654, 2003).*
Huttanus, Herbert et al., "Enhanced Colorimetric Detection of DNAs via Catalytic Aggregation of Gold Nanoparticles", Boise State University, Presentation and Abstract, NORM Jun. 25, 2012.
Dirks, Robert M. et al., "Triggered amplification by hybridization chain reaction", PNAS, vol. 101, No. 43, pp. 15275-15278 Oct. 26, 2004.
Elghanian et al; Science, vol. 277, pp. 1078-1081.
Jin et al; JACS, vol. 125; 2003; pp. 1643-1645.

* cited by examiner

*Primary Examiner* — Jehanne S Sitton
(74) *Attorney, Agent, or Firm* — McKee, Voorhees & Sease, PLC

(57) ABSTRACT

The present invention provides compositions and methods for colorimetric detection schemes for detecting a variety of biomolecules. The compositions and methods employ DNA hybridization chain reaction for catalytic aggregation of gold nanoparticles. In this catalytic aggregation scheme, a single target DNA strand triggers the formation of multiple inter-particle linkages in contrast to the single linkage formed in conventional direct aggregation schemes.

4 Claims, 5 Drawing Sheets

Specification includes a Sequence Listing.

Catalytic Aggregation Reaction Equation

Catalytic Aggregation Mechanism

Direct Aggregation (DA) Reaction Equation

SEQUENCE LISTING

```
<160> NUMBER OF SEQ ID NOS: 8

<210> SEQ ID NO 1
<211> LENGTH: 35
<212> TYPE: DNA
<213> ORGANISM: Homo sapiens

<400> SEQUENCE: 1
taacccacgc ctagactcaa agtagtctag gcgtg                                35

<210> SEQ ID NO 2
<211> LENGTH: 22
<212> TYPE: DNA
<213> ORGANISM: Homo sapiens

<400> SEQUENCE: 2
tacccacgcc tagactactt tg                                              22

<210> SEQ ID NO 3
<211> LENGTH: 18
<212> TYPE: DNA
<213> ORGANISM: Homo sapiens

<400> SEQUENCE: 3
agtctaggcg tgggttaa                                                   18

<210> SEQ ID NO 4
<211> LENGTH: 16
<212> TYPE: DNA
<213> ORGANISM: Homo sapiens

<400> SEQUENCE: 4
tcgtaggagc actggt                                                     16

<210> SEQ ID NO 5
<211> LENGTH: 16
<212> TYPE: DNA
<213> ORGANISM: Homo sapiens

<400> SEQUENCE: 5
cgtaggcggt agagat                                                     16

<210> SEQ ID NO 6
<211> LENGTH: 30
<212> TYPE: DNA
<213> ORGANISM: Homo sapiens

<400> SEQUENCE: 6
tctctaccgc ctacgaccag tgctcctacg                                      30

<210> SEQ ID NO 7
<211> LENGTH: 18
<212> TYPE: DNA
<213> ORGANISM: Homo sapiens
```

```
<400> SEQUENCE: 7
ctaggatagc ctggttaa                                                      18

<210> SEQ ID NO 8
<211> LENGTH: 18
<212> TYPE: DNA
<213> ORGANISM: Homo sapiens

<400> SEQUENCE: 8
agtctaggcg tgccatgg                                                      18
```

ENHANCED DNA SENSING VIA CATALYTIC AGGREGATION OF GOLD NANOPARTICLES BY DNA HYBRIDIZATION CHAIN REACTION

CROSS-REFERENCE TO RELATED APPLICATIONS

This is a Divisional Application of U.S. Ser. No. 14/211,076, filed Mar. 14, 2014, now U.S. Pat. No. 9,914,960, issued Mar. 13, 2018, which application claims priority under 35 U.S.C. § 119 of a provisional application Ser. No. 61/789,692, filed Mar. 15, 2013, which are hereby incorporated by reference in their entirety.

GRANT REFERENCE

This invention was made with government support under grant numbers GM093233, RR016454, and GM103408 awarded by the National Institutes of Health. The Government has certain rights in the invention.

FIELD OF THE INVENTION

The present invention relates to colorimetric read-out systems capable of detecting a variety of biomolecules, including methods and kits relating thereto. More particularly, the present invention relates to colorimetric detection that employs DNA hybridization chain reaction for catalytic aggregation of gold nanoparticles.

BACKGROUND OF THE INVENTION

Gold nanoparticle ("NP")-based colorimetric detection exploits the readily detectable color change that occurs upon NP aggregation. In some instances, NPs with appropriate surface functionalization provides for a simple and inexpensive method for sensing an expanding range of analytes such as nucleic acids, biomolecules, organic molecules, and metal ions. Gold NP-based detection methods provide several potential advantages over other techniques because 1) gold NPs have high extinction coefficients, which translates to a stronger signal and high sensitivity and 2) their color change can be detected without instrumentation.

Despite these advantages, the most common methods for nucleic acid sensing remain using fluorescent dyes and polymerase chain reaction (PCR), primarily because conventional implementation of gold NP-based in colorimetric detection restricts the sensitivity of the method. This limited sensitivity may be overcome, in some instances, by additional amplification steps. However, these additional steps undermine the simplicity of the conventional detection methods.

SUMMARY OF THE INVENTION

The present invention relates to systems, kits, and methods that allow a single target DNA to induce formation of multiple NP linkages thus significantly increasing the detection sensitivity, which may advantageously overcome sensitivity limitations of employing NPs in conventional colorimetric detection methods while also avoiding additional steps (e.g., amplification steps such as PCR).

According to the invention, engineering DNA reaction networks based on hybridization reactions, alternative linear amplifiers, cross-catalytic amplifiers, and auto-catalytic amplifiers offer an option for simple amplification of DNA strands. In general, when two gold NPs are modified with complementary oligonucleotide sequences and mixed, these nanoparticles aggregate to form complexes via hybridization of the complementary oligonucleotides (Mirkin, et al. Nature, 382, 607-609 (1996)). Throughout this disclosure, nanoparticle aggregates are alternatively referred to as complexes. Gold NP aggregation is characterized by a red-to-blue color transition that is the result of the red shifting and dampening of the nanoparticle surface plasmon resonance (SPR) band. The examples herein use several specific sequences, but it will be appreciated by one of ordinary skill in the art that other sequences are readily amenable for use in the disclosed methods.

According to the invention, oligonucleotide modifiers attached to gold NP are designed to cause aggregation of NP by either a catalytic aggregation reaction or by a direct aggregation. In either embodiment, a desired target sequence is used to create oligonucleotide linkers that are designed to cause aggregation of NPs.

Engineering DNA reaction networks based on hybridization reactions, alternative linear amplifiers, cross-catalytic amplifiers, and auto-catalytic amplifiers offer an option for simple amplification of DNA strands. In an embodiment, an entropy-driven catalytic DNA reaction network may be designed to undergo cascading reactions and amplify DNA signals. Also, through hybridization chain reactions (HCRs), double helix chains of variable lengths may be formed from two hairpin DNA strands in the presence of an initiator strand. The sensitivity of gold NP-based colorimetric detection may be enhanced by implementing a similar DNA reaction network because the number of target strands may be amplified by such a network. Systems, methods, and kits described herein may, in some embodiments, utilize HCRs for the catalytic aggregation of gold NPs, so as to enhance colorimetric detection, which may, in some instances, be a multifold increase in detection sensitivity as compared to the conventional direct aggregation schemes.

In some embodiments, gold NPs may be functionalized with either hairpin (H) or a linker:target (L:T) duplex and aggregate only in the presence of the target (T) strand. Without being limited by theory, this hybridization reaction may be considered as a reaction between stoichiometric amounts of H strand and L:T duplex triggered by catalytic amounts of the T strand forming the H:L product that links two NPs. Due to the catalytic nature of the reaction, one T strand may cause formation of multiple inter-particle linkages. NP aggregation is triggered when a T strand linearizes an H strand by toehold-mediated strand displacement. The a' domain on the H strand acts as the toehold for hybridization with the T strand. Once in a linear configuration, the c and b' domains of the H strand are exposed. Then, in the next step, the exposed c domain may act as the toehold for another strand displacement reaction that releases the T strand in L:T duplex.

Thus, multiple linkages between NPs may form for every free T strand present in the system. Thus, a target DNA in a HCR network may form an unlimited number of NP linkages.

In another embodiment a direct aggregation scheme using gold NPs is contemplated. Here two gold NPs are each functionalized with single-stranded DNA complimentary to different parts of a target DNA strand. Hybridization of both NPs to the same target effectively binds the NPs together, and the resulting NP aggregation induces a detectible change in their peak absorption magnitude and peak shift.

In yet another embodiment, the invention includes gold nanoparticles functionalized with either H or a linker:target L:T duplex configured to aggregate in a target strand. In some embodiments, target strands may be at least a portion of a biomolecule. Examples of suitable biomolecules described herein may include, but are not limited to, DNA, RNA, and the like.

In yet other embodiments, kits may comprise a set of instructions and gold nanoparticles functionalized with either H or a linker:target L:T duplex configured to aggregate in a target strand.

Further embodiments involve providing gold nanoparticles functionalized with either H or a linker:target L:T duplex configured to aggregate in a target strand; mixing the desired strand and the gold nanoparticles; aggregating a plurality of the gold nanoparticles with the desired strand so as to form at least one gold nanoparticle aggregate; and detecting the gold nanoparticle aggregate. In some embodiments, detecting may be via UV-visible spectroscopy.

While the description provided herein relates primarily to engineering DNA reaction networks, one of ordinary skill in the art should recognize the applicability to other nucleic acid based chemical reaction, e.g., locked nucleic acid (LNA), zipped nucleic acids (ZNA) peptide nucleic acids (PNA), glycol nucleic acids (GNA), and the like. For example, LNA is known to increase binding/sensing specificity between short oligos, as well as increase the mechanical and thermal stability of hybridization.

Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

FIG. 1A shows the overall reaction equation and FIG. 1B shows the reaction mechanism of catalytic aggregation reactions. Catalytic aggregation takes place between a H strand-functionalized NPs and L:T duplex-functionalized NPs in the presence of free T strands. After an inter-particle linkage is formed, the T strand is regenerated, which propagates the reaction further. FIG. 1C shows the overall reaction equation of conventional direct NP aggregation (complete base sequences shown in Table 1).

FIG. 5A shows a TEM micrograph and FIG. 5B shows UV-Vis spectrum analysis of gold nanoparticles.

DETAILED DESCRIPTION OF THE INVENTION

Figure 1A:
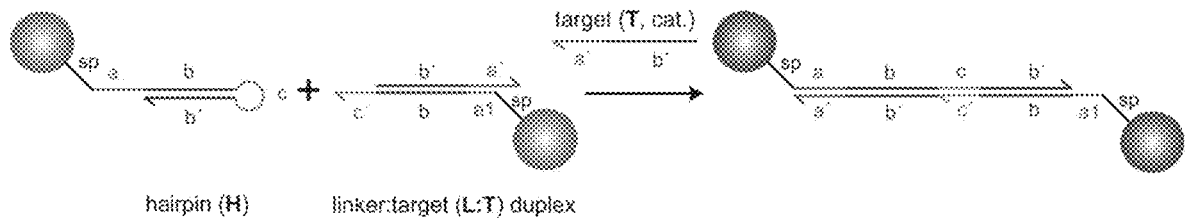
FIGS. 1A-1C illustrate catalytic and direct aggregation.

A colorimetric assay has been developed using gold NPs for the direct detection of target sequences without the need for amplification. The invention has several other advantages in addition to its high sensitivity including excellent specificity, short turnaround time, and cost effectiveness. Moreover, the use of Gold NPs eliminates the need for expensive detection instrumentation and does not require functionalization of the gold NPs, the linker, or the target.

Moreover, this assay may be adapted into a quantitative test by spectrophotometric quantification of the resulting blue color against a standard curve or developing a fluorometric version of the test by utilization of the size and distance-dependent nanoparticle surface plasmon resonance properties of Gold NPs.

Consequently, the invention permits use of gold NPs for direct detection of nuclide acids in samples and may be competitively used in place of other commercial immunoassays and RT-PCR methods.

Terms and Abbreviations

Unless explained otherwise, all technical and scientific terms used herein have the same meaning as commonly understood to one of ordinary skill in the art to which this disclosure belongs. All references herein are incorporated by reference. The following explanations of terms and abbreviations are provided to better describe the present disclosure and to guide those of ordinary skill in the art in the practice of the present disclosure.

All numbers expressing quantities of components, molecular weights, percentages, temperatures, times, length, and so forth, as used in the specification or claims are to be understood as being modified by the term "about" unless otherwise indicated.

As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

The term "sample" describes any type of sample suspected to contain a desired target sequence to be assayed for detection of such target sequence. In some embodiments a biological sample from a subject suspected of being exposed to or having condition associated with the presence of a target sequence such as viral infection, will be used, such as blood, plasma or serum, or other bodily fluids that may contain the target nucleic acid. These may include, for example, plasma, serum, spinal fluid, lymph fluid, secretions from the respiratory, gastrointestinal, or genitourinary systems including tears, saliva, milk, urine, semen, hepatocytes, and red or white blood cells or platelets. Samples may also be obtained from tissue cell culture, such as cultured hepatocytes or leukocytes, and constitute cells, including recombinant cells, or medium in which the target may be detected.

In some cases a tissue sample may be used in the assay or processed for use in the assay, for example, by a conventional method used to extract nucleic acids from the sample.

The term "purified nucleic acid" describes a nucleic acid which has been isolated from the host tissues or fluids in which the nucleic acid is normally associated, isolated from a tissue cell culture, or separated from other types of microorganisms, such as bacteria or other viruses. Techniques for isolating nucleic acids are known to those of skill in the art.

The term "preservative or additive for a sample" includes additives such as heparin or EDTA. The term also includes other agents which prevent degradation of nucleic acids or permit nucleic acids to be easily recognized in the method of the invention. These include normal saline or commercially available preservatives such as the one found in PAX gene tubes. The term "extraction buffer" refers to conventional agents and materials useful for extracting, purifying or isolating nucleic acids from a sample, such as a biological sample like serum.

The term "denaturation" refers to a process of unfolding of nucleic acids. For example, by heating a sample to 65, 75, 85, 90, 95-100° C. Denaturation may also be facilitated by addition of other ingredients such as salts, formamide, or sodium hydroxide.

The term "reaction buffer" describes a composition in which the sample, gold nanoparticles and linker nucleic acid that binds to target sequence interact. Exemplary buffers include phosphate buffer saline, and other buffers used in PCR reaction mixtures. As used herein, the term "linker" describes a polynucleotide that binds to a target nucleic acid sequence and refers to a polynucleotide which can form a hybrid structure with a sequence in a target region of the target through complementarity with a sequence in the target nucleic acid sequence. The linker will be long enough to bind to target sequences in a sample. Preferably, it will comprise 19, 20, 21, 22, 23, 24, 25, 26, 27, 28, 29, 30 or 31 bp. If the sequence is less than 19 bp, then performance will be reduced because shorter sequence will bind to non-specific sequences which would result in false positive results or if it exceeds 31 bp, then performance will be reduced because of dimerization and hairpin formation of longer polynucleotides leading also to false positive results.

For design of the linker sequences, the target sequence is divided into two sections that form a part of the design of two different linker sequences attached to separate gold NPs. In some embodiments the linker is a hairpin. Upon association with the target sequence two gold NPs become associated with a target and each other. In some embodiments, the target is then disassociated and recycled to bind another two gold NPs.

The linkers may correspond to any contiguous portion of the target nucleic acid. In one embodiment the linkers will be selected to bind to a 5' untranslated region because this region is highly conserved and can be used to differentiate between different genotypes.

The term "modified linker" describes a linker sequence that may contain one or more modified bases or contain a modification to or replacement of the phosphate backbone structure of a conventional oligonucleotide but otherwise substantially maintain its ability to hybridize to a target sequence. For example, a modification to linker sequence that increases stability or resistance to degradation or improves binding specificity or sensitivity may be made. Examples of modifications to increase nuclease resistance of the linker include the following: (a) phosphothioate modified sequence (where one of the oxygen on the phosphate of phosphodiester bond is replaced with a sulphur atom); (b) 3'-propryl group (C3 spacer, adding a propyl group at the 3' end); and (c) Inverted end (3'-3' linkage), though other modifications known to those in the art may also be employed.

For some applications linkers may contain one, two, three, four or more degenerate bases, which can base pair with A, T, G, C and/or U. Degenerate bases may be incorporated into a linker to increase its affinity for the target sequence. For example, an linker containing one, two, three, four or more degenerate bases (e.g. inosine) in its oligonucleotide sequence can be used to overcome or compensate for a mutation that may occur within the same genotype and subtype (quasispecies). Inosine resembles guanine, but without the 2-amino group, and can form stable (wobble) base pairs with adenine, cytosine and uracil that are similar in terms of interaction strength. Therefore, inosine in a probe can bind to perfectly complementary polynucleotide or ones that have mismatches at the location of the inosine to form duplex structures of comparable stability.

A linker may also be modified by conjugation to a detectable moiety, such as a fluorophore. For example, the 5' end of a linker polynucleotide sequence may be conjugated to an FAM dye whose fluorescence can be quenched by gold nanoparticles.

The term "target region" describes the portion of the sample nucleic acid to which the linker binds. For example, the target region may lie in the 5' untranslated region of genomic DNA or RNA. However, target regions from which linker polynucleotide sequences may be designed include, but are not limited to regions encoding specific epitopes, as well as control or promoter segments and non-transcribed and/or non-translated regions.

The term "target RNA" or "target DNA" refers to RNA or DNA from a sample corresponding to synthetic or genomic sequences, fragments thereof, transcripts thereof, or modified or mutant sequences. It also encompass modified or mutated genomic sequences, such as variants containing one or more single nucleotide polymorphisms, or more generally, those having a sequence containing 1, 2, 3, 4, 5 or more insertions, deletions, transpositions, or substitutions to a genomic sequence.

The term "cDNA" describes DNA complementary to RNA.

"Hybridization buffer" refers to any buffer that permits hybridization to occur between a linker sequence and a target nucleic acid, for example, 10 mM phosphate buffered saline (PBS), pH 7.0. Samples are admixed with the linker in hybridization buffer and subsequently denatured and annealed prior to admixture with gold nanoparticles. A preferred buffer is phosphate-buffered saline ("PBS"), pH 7.0-7.4. Monovalent cation (e.g., sodium or potassium) salt concentration can range from 50 mM to 300 mM. Suitable hybridization buffers and protocols are well-known in the art and are incorporated by reference to Maniatis, et al., Molecular Cloning: A Laboratory Manual, 2.sup.nd edition or Current Protocols in Molecular Biology, vol. 1 (updated October, 2010). However, salt concentration is dependent on the gold nanoparticles volume and concentration.

The term "citrate buffer" describes a buffer containing citrate used to prepare or suspend the colloidal gold nanoparticles (Gold NPs). Alternatively, a buffer containing hydrazine, L-tryptophan, an alcohol, especially a lower $C_1$-$C_6$ alcohol, an ether, or sodium diphenyl aminosulfonate may be used. A preferred salt is trisodium citrate salt at a concentration of 30-50 mM or 1-2 wt % (no specific pH). Suitable buffers and methods for making and using colloidal gold are incorporated by reference to John Turkevich. Colloidal gold. Part I. Gold Bull. 1985; 18(3): 86-92; John Turkevich. Colloidal gold. Part II. Gold Bull. 1985; 18(4):125-131; and Katherine C. Graber, R. Grissith Freeman, Micheal B. Hommer, Micheal J. Natan. Preparation and characterization of gold colloid monolayers. Analytical Chemistry 1995; 67(4): 735-743.

The term "gold nanoparticle" refers to spherical gold nanoparticles. Generally, the gold nanoparticles are produced by citrate reduction method and have an average diameter ranging from 2.0 nm to 100 nm, preferably, an average diameter ranging from 10 to 35 nm, and more preferably from 15 to 30 nm. When the size of the gold nanoparticle is too small, then performance is reduced because surface-plasmon resonance would be reduced and completely abolished for particles <2 nm and the color change will not be observed and when it is too large, then performance is reduced because the aggregation affinity of the nanoparticles would be higher leading to false positive results.

The gold nanoparticles used in the invention may be produced or synthesized by methods known in the art, such as those described above in the background section. Alternatively, exemplary methods include (a) by reduction of chloroauric acid with sodium borohydride; (b) by reduction of chloroauric acid with hydrogen peroxide; or (c) by a single phase microemulsion method. These methods of producing gold nanoparticles are hereby incorporated by reference to the articles cited above.

"Fluorometric detection" refers to a method in which a fluorescent dye, such as a fluorescein derivative like fam (fluorescein amidite) dye or other fluorophore, has been conjugated to the 5'end of the linker sequence as described above and used to develop a Forster resonance energy transfer (FRET)-based detection assay. For example, an fam molecule is quenched in the absence of the target nucleic acid sequence by the gold nanoparticles, while in the presence of target sequence, hybridization occurs between the linker and the target and so, the linker sequence is detached from the gold nanoparticles and hybridizes to the target complementary sequence. Fam emission becomes detectable and indicates presence of the target.

"Colorimetric detection" refers to a method in which the sample once contacted with the linker, denatured, and annealed is mixed with a colloidal gold containing gold nanoparticles and a colorimetric determination is performed where a red-to-blue shift in solution color indicates the presence of target sequence complementary to the linker. When the color of the mixture remains red it indicates the absence of target sequence complementary to the linker. Thus, the presence of the target is detected colorimetrically by a change in color from red to blue where gold nanoparticles aggregate in presence of the target:linker complexes in comparison with a negative control or a sample not containing the target sequence where nanoparticles do not aggregate and no color change is observed.

The examples herein use several specific sequences, but it will be appreciated by one of ordinary skill in the art that other sequences are readily amenable for use in the disclosed methods.

The term "kit" refers to a composition of matter containing one or more ingredients necessary to practice the method of detecting a target nucleic acid sequence according to the invention. Preferably, the kit will contain gold nanoparticles and a polynucleotide that binds to a specific target sequence, such as a virus sequence, bacterial sequence or any other nucleic acid sequence the presence of which is desired to be known in a test sample.

A kit may also contain at least one biological sample preservative or additive for a sample, such as an agent that prevents degradation of nucleic acid, an extractant buffer for extracting, isolating or purifying nucleic acid sequences from a sample, a reaction buffer in which gold nanoparticles, the linker polynucleotide binding to target nucleic acid, and the biological sample are mixed, a negative control sample, a positive control sample, one or more reaction containers, such as tubes or wells, a colorimetric chart, a packaging material, an instruction for use in detecting the same.

The detection method of the invention comprises contacting a sample in which the presence or absence of a target nucleic acid sequence is desired to be known with a pair of linker polynucleotides (or modified linkers) that bind the target. Usually the test nucleic acid will be extracted or purified from a sample and denatured prior to mixing it with the linkers, and the concentration of linker and salt are carefully selected to permit hybridization as well as subsequent discrimination of samples containing hybridized target and linker from samples not containing the target sequence after admixture with gold nanoparticles. As noted above, other assay ingredients comprise the linker, a suitable buffer such as a salt-containing hybridization buffer, the sample, and the gold nanoparticles.

Nucleic acid material suspected of containing the target sequence may be extracted from a clinical specimen using a commercial extraction kit, such as those available from Promega. To eliminate hybridization to cell-free DNA or other contaminating DNA, a sample may be treated with DNAse prior to hybridization to a linker. Denaturation and annealing of a sample may be performed by methods known in the art, such as by use of a thermal cycler, heat block, or water bath. For example, the sample may be denatured at 95° C. and annealed at 60° C. for 1 minute for both steps in PBS buffer at pH 7.0-7.4.

The extracted or purified sample can be diluted with a sample buffer such as PBS or Tris prior to contacting it with a suitable linker sequence. The target nucleic acid in a sample and the linker are hybridized under conditions that do not affect the stability of gold colloid or that interfere with sample hybridization to the linker.

The extracted or purified sample can be diluted with a sample buffer such as PBS or Tris prior to contacting it with a suitable linker sequence, Importantly, it is not necessary to amplify the nucleic acid from the sample for this assay.

The nucleic acid in a sample and the linker can be hybridized before the addition of gold nanoparticles as described herein under conditions that do not interfere with sample hybridization to the linker or subsequently affect the stability of gold colloid used in the colorimetric detection step. Depending on the type of test sample an appropriate ratio of sample to linker sequences is selected, usually a sample will be contacted with about 500-1,000 nM of linker and permitted to hybridize for a suitable time, for example, for 1-3 min, at a temperature ranging from 45 to 60 degrees or at room temperature.

While the ratio of linker to gold nanoparticle content may vary depending on the size of the gold nanoparticles, each gold nanoparticle may be stabilized from salt-induced aggregation when it is covered by about a minimum of 12 linker up to 100 molecules. One example of a suitable ratio of target, linker and gold nanoparticles would be 7 microliters of extracted RNA of unknown or variable concentration in combination with 1 µM linker which is admixed with 10 nM gold nanoparticles.

The concentration of gold nanoparticles is also selected to provide a sensitive discrimination of samples containing duplex target sequences and linkers from those not containing the target sequence. As a rough estimate, about 7 to 100 molecules of linker can stabilize a gold nanoparticle and prevent its aggregation. The presence of the target in a sample will be detected by a colorimetric change which can be visually determined or determined using an instrument.

The sample once contacted with the linker, denatured, and annealed is mixed with a colloidal gold containing gold nanoparticles and a colorimetric determination is performed where a red-to-blue shift in solution color indicates the presence of target nucleic acid complementary to the linker. When the color of the mixture remains red it indicates the absence of sequence complementary to the linker. Thus, the target is detected colorimetrically by a change in color from red to blue where gold nanoparticles aggregate in presence of the target:linker duplexes in comparison with a negative control or a sample not containing the virus where nanoparticles do not aggregate and no color change is observed.

Alternatively, the presence of target sequence hybridized to an linker can be performed using a modified linker that has been tagged with a fluorescent dye, such as with FAM dye at its 5' terminal, and whose fluorescent emission is quenched when bound to a gold nanoparticle. In this case, the presence of a sequence complementary to the linker, will result in a fluorescent signal while samples lacking sequence complementary to the linker will have their fluorescent emissions quenched by binding to the gold nanoparticles.

The present invention relates to systems, kits, and methods that allow a single target DNA to form multiple NP linkages thus significantly increasing the detection sensitivity, which may advantageously overcome sensitivity limitations of employing NPs in conventional colorimetric detection methods while also avoiding additional steps (e.g., amplification steps such as PCR). Without being limited by theory it is believed that engineering DNA reaction networks based on hybridization reactions, alternative linear amplifiers, cross-catalytic amplifiers, and auto-catalytic amplifiers offer an option for simple amplification of DNA strands. For example, an entropy-driven catalytic DNA reaction network may be designed to undergo cascading reactions and amplify DNA signals. Also, through HCR, double helix chains of variable lengths may be formed from two hairpin DNA strands in the presence of an initiator strand. The sensitivity of gold NP-based colorimetric detection may be enhanced by implementing a similar DNA reaction network because the number of target strands may be amplified by such a network. Systems, methods, and kits described herein may, in some embodiments, utilize HCRs for the catalytic aggregation of gold NPs, so as to enhance colorimetric detection, which may, in some instances, be a multifold increase in detection sensitivity as compared to the conventional direct aggregation schemes.

Figure 1B:
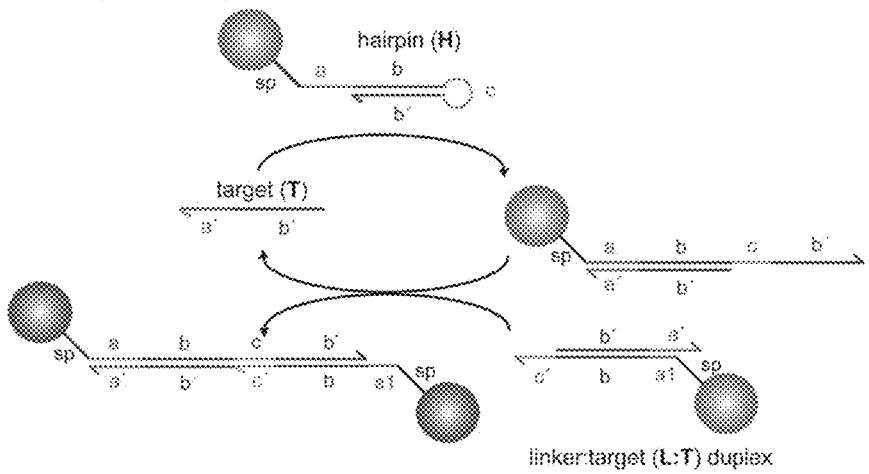

In some embodiments, the overall reaction of the catalytic aggregation scheme may be that illustrated in the reaction equation of FIG. 1A and the reaction mechanism of FIG. 1B. As illustrated in FIG. 1A, in some embodiments, gold NPs may be functionalized with either hairpin (H) or a linker:target (L:T) duplex and aggregate only in the presence of the target (T) strand. Without being limited by theory, this hybridization reaction may be considered as a reaction between stoichiometric amounts of H strand and L:T duplex triggered by catalytic amounts of the T strand forming the H:L product that links two NPs. Due to the catalytic nature of the reaction, one T strand may cause formation of multiple inter-particle linkages. As illustrated in FIG. 1B, NP aggregation may, in some embodiments be triggered when a T strand linearizes an H strand by toehold-mediated strand displacement. Again with theoretical limitation, it is believed that in this step the a' domain on the H strand acts as the toehold for hybridization with the T strand. Once in a linear configuration, the c and b' domains of the H strand are exposed. Then, in the next step, the exposed c domain may act as the toehold for another strand displacement reaction that releases the T strand in L:T duplex. It is believed that two important events take place in this second operation: A linkage between two NPs is formed and a new T strand is released, which can reinitiate the entire sequence of DNA reactions thus propagating and enhancing NP aggregation. As a result, multiple linkages between NPs may form for every free T strand present in the system. Therefore, it is believed that, in some embodiments, a target DNA in a HCR network may form an unlimited number of NP linkages. Thus, the combination of a HCR network with gold NPs may, in some embodiments, be utilized as a system for catalytic aggregation in high-sensitivity colorimetric detection.

Figure 1C:
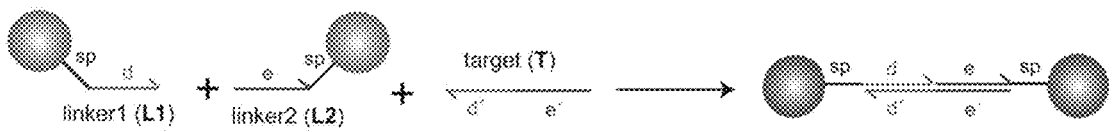

Alternatively, a direct aggregation scheme using gold NPs is typically composed of two different types of gold NPs, each functionalized with single-stranded DNA complimentary to different parts of a target DNA strand, as illustrated in FIG. 1C. Hybridization of both NPs to the same target effectively binds the NPs together, and the resulting NP aggregation induces a detectable change in their peak absorption magnitude and peak shift. In such conventional direct aggregation designs, target DNA is able to form only a single inter-particle linkage, which limits the sensitivity of this method.

In some embodiments, systems may comprise gold nanoparticles functionalized with either H or a linker:target L:T duplex configured to aggregate in a target strand. In some embodiments, target strands may be at least a portion of a biomolecule. Examples of suitable biomolecules described herein may include, but are not limited to, DNA, RNA, and the like.

In some embodiments, kits may comprise a set of instructions and gold nanoparticles functionalized with either H or a linker:target L:T duplex configured to aggregate in a target strand.

Some embodiments may involve providing gold nanoparticles functionalized with either H or a linker:target L:T duplex configured to aggregate in a target strand; mixing the desired strand and the gold nanoparticles; aggregating a plurality of the gold nanoparticles with the desired strand so as to form at least one gold nanoparticle aggregate; and detecting the gold nanoparticle aggregate. In some embodiments, detecting may be via UV-visible spectroscopy.

While the description provided herein relates primarily to engineering DNA reaction networks, one of ordinary skill in the art should recognize the applicability to other nucleic acid based chemical reaction, e.g., locked nucleic acid (LNA), zipped nucleic acids (ZNA) peptide nucleic acids (PNA), glycol nucleic acids (GNA), and the like. For example, LNA is known to increase binding/sensing specificity between short oligos, as well as increase the mechanical and thermal stability of hybridization.

While the description provided herein relates primarily to engineering DNA reaction networks based on hybridization reactions, one of ordinary skill in the art should understand the applicability of merging nanoparticle aggregation with other chemical reaction networks (e.g., alternative linear amplifiers, cross-catalytic amplifiers, and auto-catalytic amplifiers), including any necessary modifications for such applications.

In some embodiments, other suitable nanoparticles may be used in place of gold nanoparticles. For example, other suitable nanoparticles may include silver nanoparticles, nanoparticles with a gold shell, nanoparticles with a silver shell, and the like.

In some embodiments, other suitable molecular dyes or fluorescent metallic clusters may be used in place of gold nanoparticles. For example, suitable molecular dyes or fluorescent metallic clusters may include those that show quenching effects based on proximity changes.

The Examples below are provided only for illustrative purposes and not to limit the scope of the present invention. Numerous embodiments within the scope of the claims will be apparent to those of ordinary skill in the art, thus the following non-limiting examples only describe particular embodiments of the invention. The present invention relates to colorimetric read-out systems capable of detecting a variety of biomolecules, including methods and kits relating thereto.

To facilitate a better understanding of the present invention, the following examples of preferred or representative embodiments are given. In no way should the following examples be read to limit, or to define, the scope of the invention.

EXAMPLES

Figure 5A:
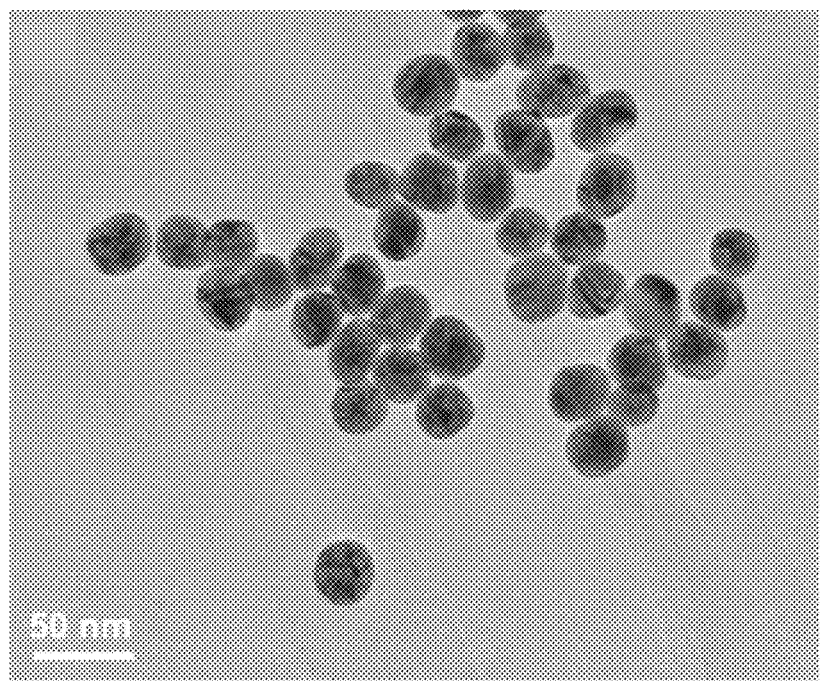
FIGS. 5A-5B show analysis of gold nanoparticles according to at least one embodiment described herein.
Figure 5B:
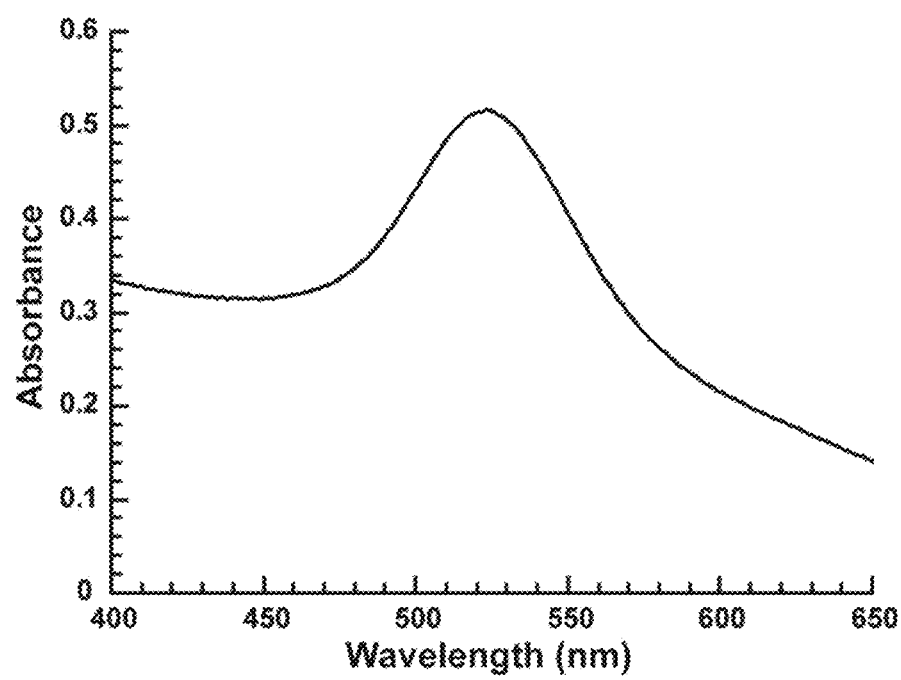

Spherical gold nanoparticles of approximately 25 nm in diameter were synthesized by the reduction of gold chloride using sodium citrate. A transmission electron micrograph and UV-visible spectrum are included in FIG. 5. Briefly, 100 mL of 0.25 mM $HAuCl_4$ was heated to a boil and 1 mL of sodium citrate (0.51 mM) was added with vigorous stirring. The solution was heated for an additional 15 min and then allowed to cool to room temperature. The size of NPs was measured using TEM and UV-Vis spectroscopy. Thiolated DNA strands, obtained from Integrated DNA Technologies, were first reduced using 0.1 M dithiothreitol (DTT) solution to cleave disulfide bonds, followed by an elution through a desalting column (NAP-10, GE healthcare) to remove unreacted DTT. Following quantification by absorbance measurements at 260 nm, DNA strands were mixed with gold NPs in a 500:1 ratio and phosphate buffer concentration was increased to 10 mM and pH 7.4 along with 0.01% (w/w) sodium dodecylsulfate (SDS). Following an overnight incubation, NaCl concentration was gradually brought up to 0.3 M over 2 hours by additions of 4 M NaCl. The NPs were then further purified by centrifugation (three times at 10000 rpm for 15 min) to remove any unreacted excess DNA strands. After each centrifugation, the NP pellet was redispersed in 10 mM phosphate buffer (pH 7.4, 0.01% (w/w) SDS, and 0.3 M NaCl) and the NP concentration was determined by measuring absorbance at 525 nm. The hybridization of target (T) strand to linker (L) strand bound to NPs were accomplished by overnight incubation of L strand-functionalized NPs with 500 times excess of T strand followed by purification by centrifugation to remove excess unreacted T strands.

For each aggregation reaction, three reagents—the two complimentary types of functionalized NPs and the target—were mixed in a plastic cuvette sealed with paraffin film. All aggregation reactions were conducted in 10 mM phosphate buffer (pH=7.4) with 0.3 M NaCl and 0.01% (w/w) SDS. Each 400 µL sample had a final Gold NP concentration of 314 pM (157 pM of each type of NP). The T strand concentrations are multiples of 157 pM. Absorbances for each reaction were measured at 0, 1, 2, 4, 8, and 20 hours from the time of mixing all reagents.

Hybridization reactions of DNA strands used for gel electrophoresis were carried out in 10 mM phosphate buffer (pH 7.4), 0.01% SDS (w/w) and 0.3 M NaCl. Each hybridization reaction was allowed to sit at room temperature for 4 hours before being loaded into the gels. The gel composition was 3% agarose in 1× TAE buffer with 5 µg/mL ethidium bromide. The gels were run at 100 V for 45 min.

Catalytic aggregation (CA) of gold nanoparticles provides significantly greater detection sensitivity compared to direct aggregation (DA) through the formation of multiple NP linkages from a single target DNA strand. The overall reaction of the CA scheme is illustrated in the reaction equation of FIG. 1(a) and the reaction mechanism of FIG. 1(b). Gold NPs are functionalized with either hairpin (H) or a linker:target (L:T) duplex and aggregate only in the presence of the target (T) strand. This hybridization reaction can be considered as a reaction between stoichiometric amounts of H strand and L:T duplex triggered by catalytic amounts of the T strand forming the H:L product that links two NPs. Due to the catalytic nature of the reaction, one T strand can cause formation of multiple inter-particle linkages. As illustrated in FIG. 1(b), NP aggregation is triggered when a T strand linearizes an H strand by toehold-mediated strand displacement. In this step, the a' domain on the H strand acts as the toehold for hybridization with the T strand.(Yurke et al. 2000; Zhang and Winfree 2009) Once in a linear configuration, the c and b' domains of the H strand are exposed. In the next step, the exposed c domain acts as the toehold for another strand displacement reaction that releases the T strand in L:T duplex. Two important events take place in this second operation: A linkage between two NPs is formed and a new T strand is released, which can reinitiate the entire sequence of DNA reactions thus propagating and enhancing NP aggregation. As a result, multiple linkages between NPs can form for every free T strand present in the system. In principle, a target DNA in a HCR network can form an unlimited number of NP linkages. Thus, the combination of a HCR network with gold NPs creates a system capable of catalytic aggregation for high-sensitivity colorimetric detection.

On the other hand, DA scheme using gold NPs is composed of two different types of gold NPs, each functionalized with single-stranded DNA complimentary to different parts of a target DNA strand, as illustrated in FIG. 1(c). Hybridization of both NPs to the same target effectively binds the NPs together, and the resulting NP aggregation induces a detectible change in their peak absorption magnitude and peak shift. In such conventional DA designs, target DNA is able to form only a single inter-particle linkage, which limits the sensitivity of this method.

The CA design involves a 40 nucleotide (nt) hairpin strand (H) and a linker (L, 25 nt): target (T, 18 nt) duplex. The domain lengths are specified in FIG. 1 and the base sequences of all DNA strands are listed in Table 1. Instead of two hairpin strands used for the original HCR, a hairpin strand (H) and a duplex (L:T) were used to alleviate steric hindrance between NPs that arises when the more than two NPs were linked into a single DNA chain. Also, an extra domain (a1, 3 nt) that is complementary to half of the a' domain was included to minimize reactions between L strand-bound T strands with H strands by sequestering a portion of the a domain and provide the advantage to free T strands in hybridizing with H strands. To compare the performance of the CA designs against a conventional colorimetric detection scheme, a DA scheme was also tested. DNA strands used for the DA scheme are composed of 12 nt spacer (sp) and 15 nt active domains (d and e). The inter-particle distance of NP aggregates produced from DA scheme is 54 bp, which is similar to that of CA (47 bp).

TABLE 1

Sequences of DNA strands

| Strands | Sequence |
|---|---|
| CA H | 5'-/thiol/$T_4$AACCCACGCCTAGACTCAAAGTAGTCTAGGCGTG-3' (SEQ ID NO: 1) |
| CA L | 5'-/thiol/$T_4$ACCCACGCCTAGACTACTTTG-3' (SEQ ID NO: 2) |
| CA T | 5'-AGTCTAGGCGTGGGTTAA-3' (SEQ ID NO: 3) |
| DA L1 | 5'-/thiol/$T_{12}$CGTAGGAGCACTGGT-3' (SEQ ID NO: 4) |
| DA L2 | 5'-CGTAGGCGGTAGAGAT$_{12}$/thiol/-3' (SEQ ID NO: 5) |
| DA T | 5'-TCTCTACCGCCTACGACCAGTGCTCCTACG-3' (SEQ ID NO: 6) |
| C1 | 5'-CTAGGATAGCCTGGTTAA-3' (SEQ ID NO: 7) |
| C2 | 5'-AGTCTAGGCGTGCCATGG-3' (SEQ ID NO: 8) |

Figure 2A:
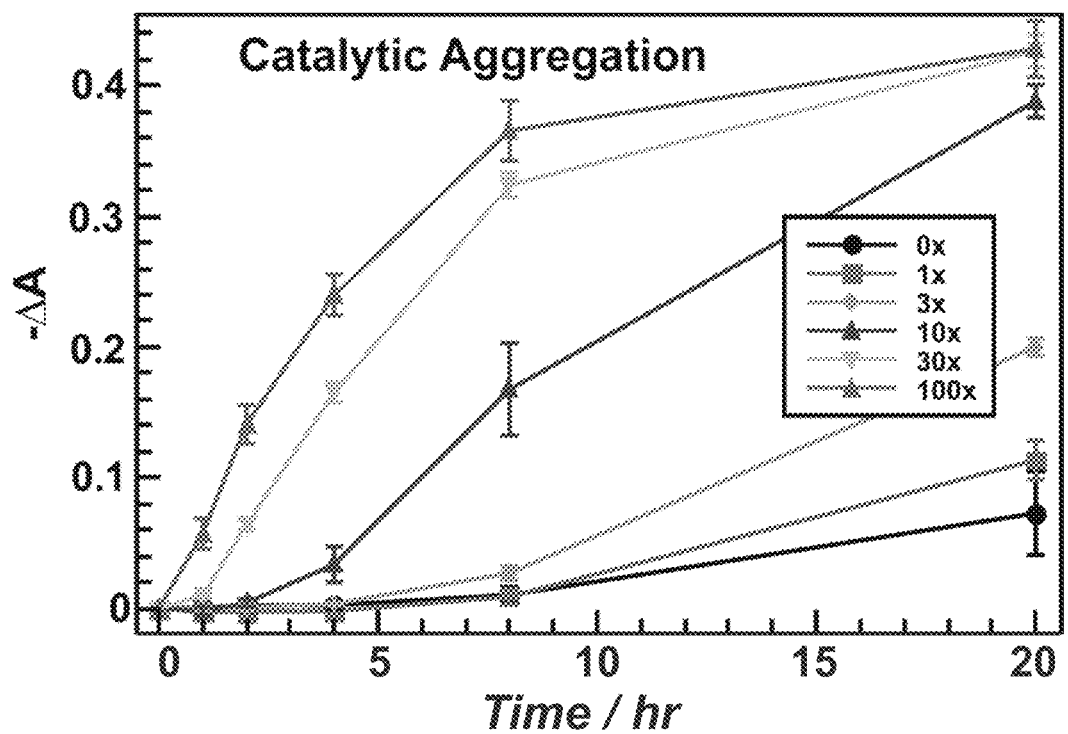
FIGS. 2A-2B show absorbance change as a function of target concentration and time for (FIG. 2A) catalytic aggregation and (FIG. 2B) direct aggregation schemes. The catalytic aggregation (CA) scheme exhibit detectable signal at 3× and 10× while direct aggregation (DA) scheme does not show any signal at those target concentrations.
Figure 2B:
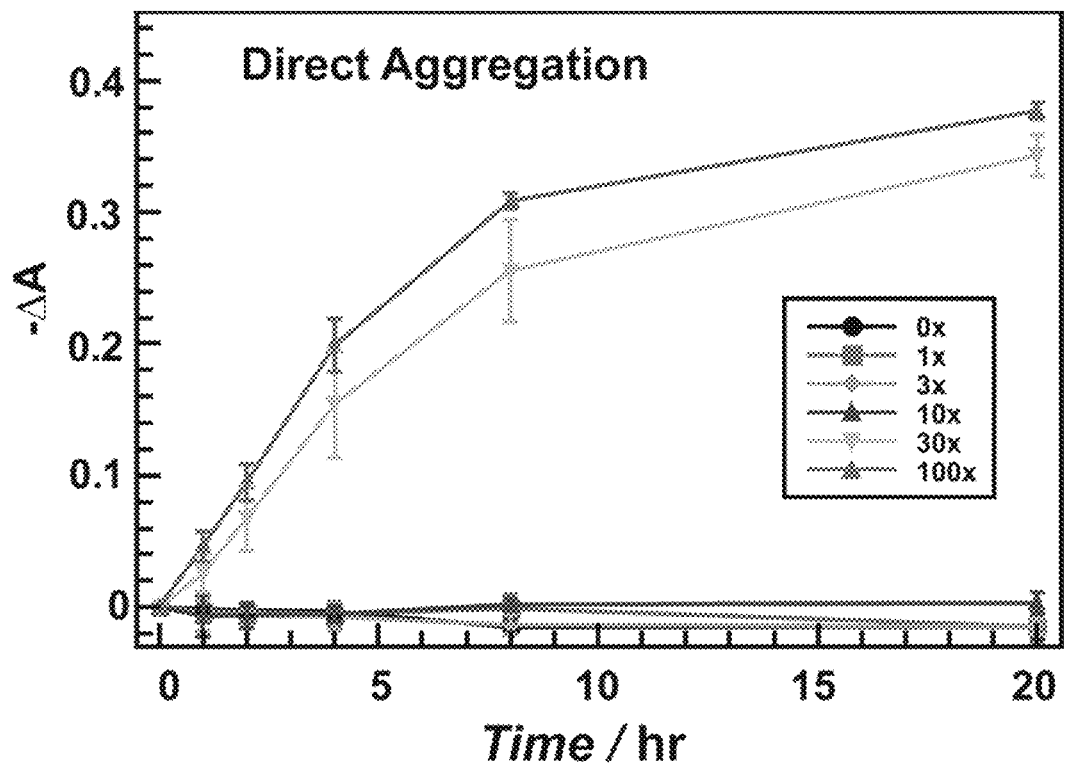

NP aggregation experiments of the catalytic aggregation scheme were conducted by adding varying amounts of target strand to a 1:1 mixture of H strand-functionalized NPs and L:T duplex-functionalized NPs. Gold NPs with ~25 nm diameter were synthesized using citrate reduction method, and DNA functionalization was accomplished through thiol groups present at the ends of DNA strands. The decreases of UV-vis peak absorbance (−ΔA) and the peak shifts (FIG. 3) for each sample were used as a metrics to quantify the extent of NP aggregation. The target concentrations in FIG. 2 are multiples of 157 pM (1×=157 pM). As shown in FIG. 2(a) the catalytic aggregation scheme exhibited detectable ΔA at low (1×, 3×, and 10×) target concentrations, whereas ΔA from the direct aggregation scheme at such low target concentrations were either absent (1× and 3×) or minimal (10×). These results indicate that measurable NP aggregation takes place even at low target DNA levels due to the catalytic nature of catalytic aggregation schemes. While the number of inter-particle linkages in direct aggregation scheme was not sufficient to cause detectable change in their optical properties, in the catalytic aggregation scheme, changes in optical properties are observed because more inter-particle linkages were formed for every T strand, hence enhancing the overall sensitivity of colorimetric detection. 1× and 10× samples in catalytic aggregation scheme exhibit similar level of −ΔA to 10× and 30× samples in direct aggregation scheme after 20 hrs, respectively. These results suggest that between three to ten-fold increase of sensitivity was achieved at those concentrations. As expected, ΔA from direct aggregation samples significantly increased at higher (30×and 100×) target concentrations to levels comparable to the catalytic aggregation scheme because sufficient amounts of T strands were present to cause extensive NP aggregation even without T strand regeneration (FIG. 2(b)). The impact of higher T strand concentration on NP aggregation in the catalytic aggregation schemes was diminished because further aggregation induced by extra T strands in higher concentration had less impact on the optical properties of the NPs. The catalytic aggregation scheme exhibited slight NP aggregation even in the absence of the T strand, as evidenced by ΔA in a negative control (0×) sample (FIG. 2(a)). This shift indicates that the DNA hybridization reaction can be initiated by not only free T strands but also by T strands from the L:T duplex. Partial protection of a' domain by a1 domain and steric hindrance between NPs in such instances proved insufficient to completely suppress such unintended initiation.

Figure 3A:
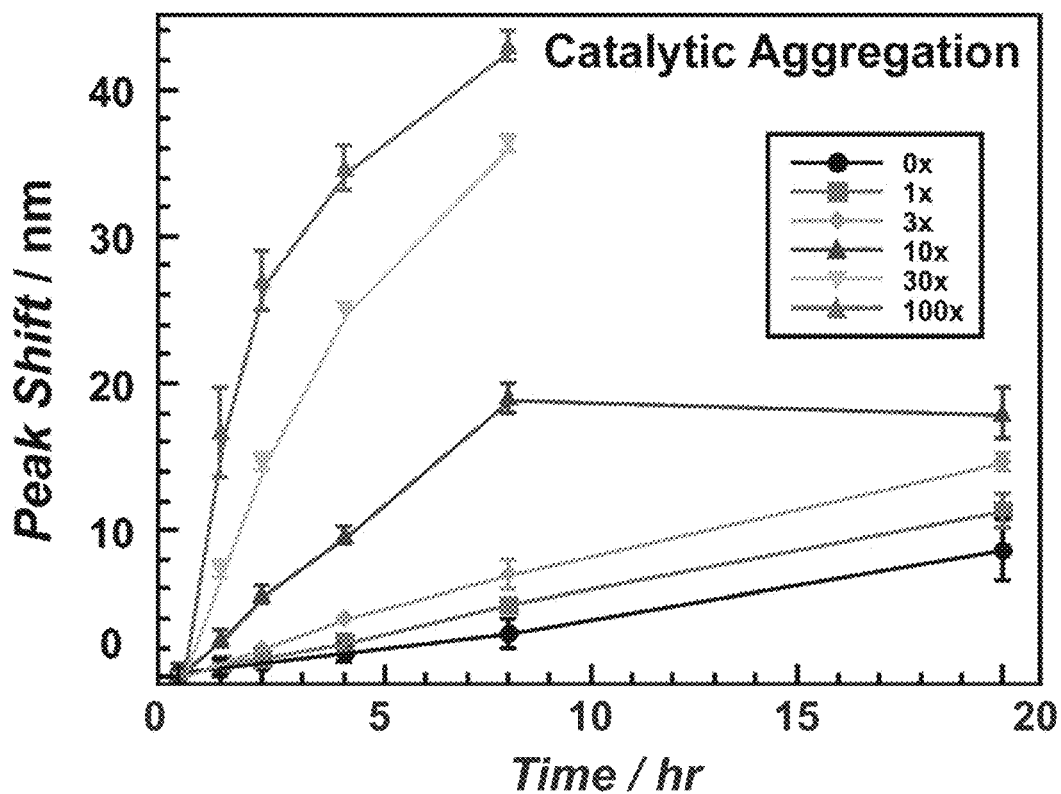
FIGS. 3A-3B show absorption peak shift as a function of target concentration and time for (FIG. 3A) catalytic aggregation and (FIG. 3B) direct aggregation schemes. The CA scheme exhibit detectable signal at 1× and 3× while DA scheme does not show any signal at those target concentrations.
Figure 3B:
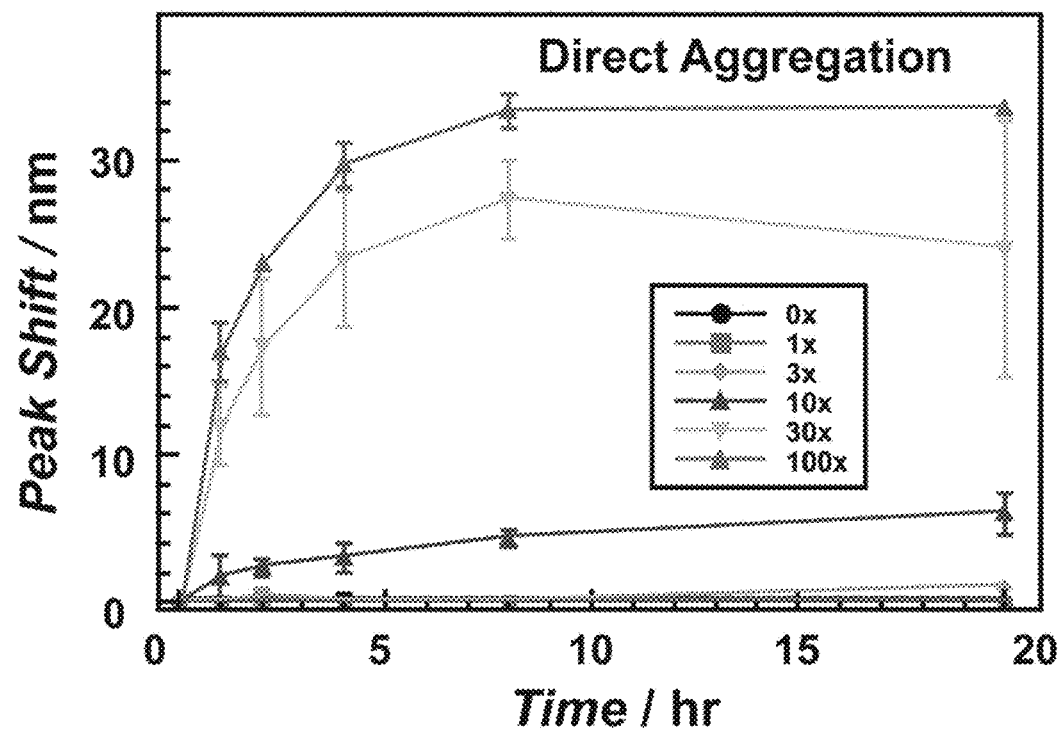

To verify the correct operation of the catalytic aggregation scheme, agarose gel electrophoresis of the DNA strands without NPs was performed. The DNA strands were incubated for 4 hrs prior to the electrophoresis, which was carried out in a 3% agarose gel at 100 V for 45 min. The agarose gels were stained with ethidium bromide to label double-helix bands. Two major bands were observed from the catalytic aggregation sample (FIG. 3A). The lower molecular weight band (lower band) represents the mixture of H strands and L:T duplexes. The higher molecular weight band (upper band) represents the H:L product that links two NPs together. In catalytic aggregation scheme, the product band became significant at 0.3× target concentration. In the direct aggregation scheme, no appreciable double helix band was observed at low concentrations with a faint band appearing at 0.3× target concentration. These gel electrophoresis results verify that the H:L product, hence inter-particle linkages, form at much lower T strand concentrations in the catalytic aggregation scheme.

Figure 4B:
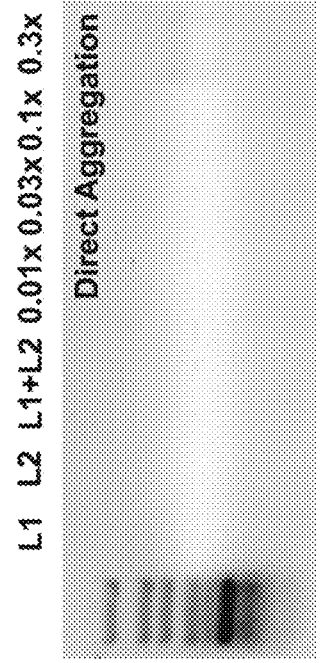
FIGS. 4A-4D show agarose gel electrophoresis results of DNA strands used in (FIGS. 4A and 4C) CA and (FIGS. 4B and 4D) DA schemes. In the CA scheme, a distinct product band was observed when the T strand concentration was as low as 0.3×. Absorbance decrease at 4 hrs with 30× concentration of specific and non-specific target strands. In the CA scheme, maximum ΔΔ values were induced by the target (T) strands specific to the scheme.
Figure 4D:
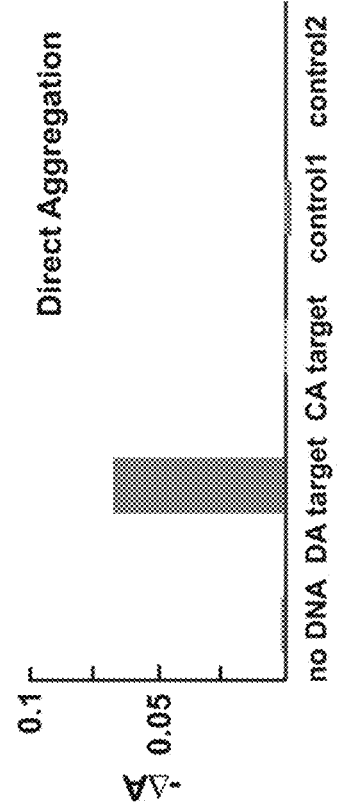
Figure 4A:
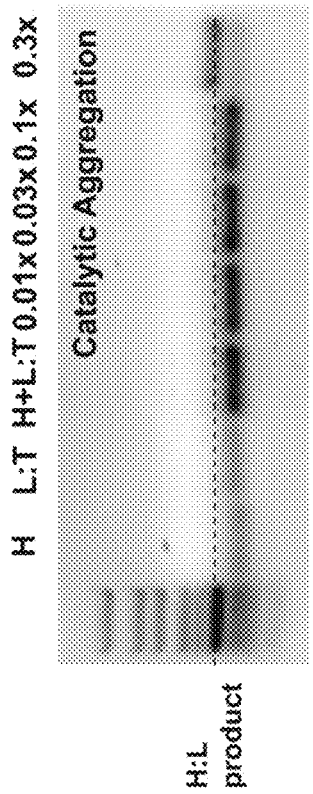
Figure 4C:
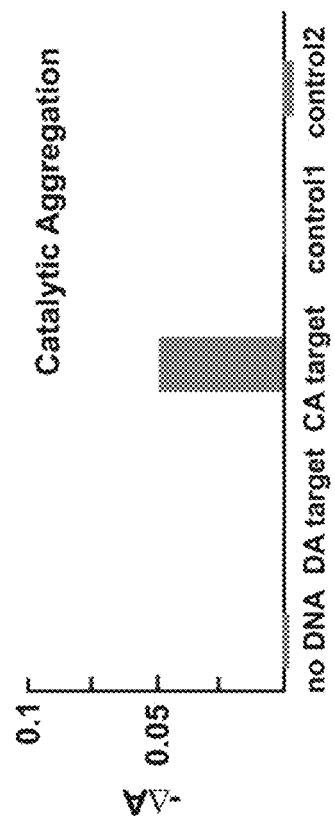

To test target specificity, aggregation experiments of the two aggregation schemes were conducted with each of four DNA strands at 30× concentrations and 4 hr reaction times (FIGS. 3A and B). The four strands were T strands for direct aggregation, catalytic aggregation and two control strands (C1 and C2). The control strands were designed such that they have random non-specific base sequences either in a' or b' domain of the T strand. For example, the Control 1 (C1) strand has the same toehold region (domain a' in FIG. 1B) as the T strand while the rest of the sequence is not identical to the b' domain of the T strand. The Control 2 (C2) strand has a random toehold region (a' domain) while the b' domain is identical to the T strand. The results of experiments carried out at a 30× target concentration and a 4 hr incubation are summarized in FIGS. 4C and D. In each design, the correct target strand caused the largest absorbance decrease. The peak shifts from control target strands were comparable to those exhibited by samples without target strands. These results indicate that the catalytic aggregation schemes are very specific, and the DNA strand that can both attach to the toehold and open the hairpin are necessary to initiate NP aggregation.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention.

What is claimed is:

1. A kit comprising:
   a first gold nanoparticle comprising a first linker sequence which will hybridize to a contiguous target sequence a' and b', wherein said first linker sequence has a thiol group on the 3' or 5' end, and comprises: (i) a sequence a which is the complement of said target sequence a', (ii) sequence b which is the complement of said target sequence b', (iii) a b' sequence, and (iv) a hairpin loop with sequence c which is formed by hybridization of sequences b and b' in absence of said target sequence a' and b'; and
   a second gold nanoparticle comprising a second linker sequence, wherein said second linker sequence will hybridize to a contiguous target sequence a' and b' and comprises (i) the complement of said target sequence b', (ii) a less than full length complement of said target sequence a', and (iii) the complement of said hairpin loop with sequence c, and does not form a hairpin in the presence or absence of the target sequence, and
   optionally, an RNA extractant buffer, a reaction buffer, a negative control sample, a positive control sample, a reaction container, a colorimetric chart, a packaging material, at least one biological sample preservative or additive, or a combination thereof; and
   instructions for use in detecting said target sequence.

2. A gold nanoparticle aggregate comprising:
   (a) a target sequence with continuous sequences a' and b';
   (b) a gold nanoparticle comprising a spacer group and a first linker, wherein said first linker has a thiol group on the 3' or 5' end and is capable of hybridizing to said target, said first linker comprising:
      i) sequence a which is the complement of target sequence a',
      ii) sequence b which is the complement of target sequence b',
      iii) a b' sequence, and
      iv) a hairpin loop with sequence c which is formed by hybridization of sequences b and b' in absence of said target; and
   (c) a second linker comprising a complement of the first linker and a complement of said target, wherein in the presence of said target, said first linker aggregates with said second linker, and wherein said second linker does not form a hairpin in the presence or absence of said target.

3. The gold nanoparticle aggregate of claim 2 wherein said first linker and/or second linker includes a modification to increase stability of the linker sequences.

4. The gold nanoparticle aggregate of claim 2 wherein said target sequence is approximately 20 nucleotides in length.

* * * * *